US006110154A

United States Patent [19]

Shimomura et al.

[11] Patent Number: 6,110,154

[45] Date of Patent: Aug. 29, 2000

[54] VALVE AND VALVED TROCAR JACKET TUBE

[75] Inventors: Kazuyuki Shimomura, 23-31, Shakujii-dai 8-chome, Nerima-ku, Tokyo; Yukihiko Tamai, Nagano-ken, both of Japan

[73] Assignees: Hakko Electric Machine Works, Co. Ltd.; Kazuyuki Shimomura, both of Japan

[21] Appl. No.: 08/946,993

[22] Filed: Oct. 8, 1997

[30] Foreign Application Priority Data

Oct. 8, 1996 [JP] Japan .................................... 8-266883

[51] Int. Cl.[7] ...................................................... A61M 5/14

[52] U.S. Cl. .......................... 604/256; 604/246; 604/104; 604/264

[58] Field of Search .................................... 604/256, 246, 604/513, 93, 104, 105, 174, 264, 268, 278, 913; 251/143; 128/887

[56] References Cited

U.S. PATENT DOCUMENTS

| | | | |
|---|---|---|---|
| 5,127,626 | 7/1992 | Hilal et al. | 251/149.1 |
| 5,334,164 | 8/1994 | Guy et al. | 604/248 |
| 5,350,364 | 9/1994 | Stephens et al. | 604/167 |
| 5,360,417 | 11/1994 | Gravener et al. | 604/278 |
| 5,366,478 | 11/1994 | Brinkerhoff et al. | 660/213 |
| 5,389,081 | 2/1995 | Castro | 604/167 |
| 5,391,154 | 2/1995 | Young | 604/167 |
| 5,492,304 | 2/1996 | Smith et al. | 251/149.1 |
| 5,514,133 | 5/1996 | Golub et al. | 606/1 |
| 5,545,179 | 8/1996 | Williamson, III | 606/213 |
| 5,741,298 | 4/1998 | MacLeod | 606/213 |

*Primary Examiner*—Corrine McDermott
*Assistant Examiner*—Cris L. Rodriguez
*Attorney, Agent, or Firm*—Rogers & Killeen

[57] ABSTRACT

A valve and and a valved trocar jacket tube by which there is no need of an adapter, types of a clamp or the like to be used are not limited, and leakage of an inert gas from an abdominal cavity can be prevented. In the valve and the valved trocar jacket tube, when a pair of rings are relatively rotated at a predetermined angle in the opposite directions, a cylindrical section in a rubber-like member is opened. In case of employing a clamp or the like, it is inserted into the abdominal cavity through the opened cylindrical section. Since the rubber-like member has elasticity, the cylindrical section is close together with the clamp or the like inserted.

14 Claims, 9 Drawing Sheets

100A
10
13
13a
13c
12a
13b
12b 12
13b
11b 11
11a
102
P
101a
Pa
101

FIGURE 11
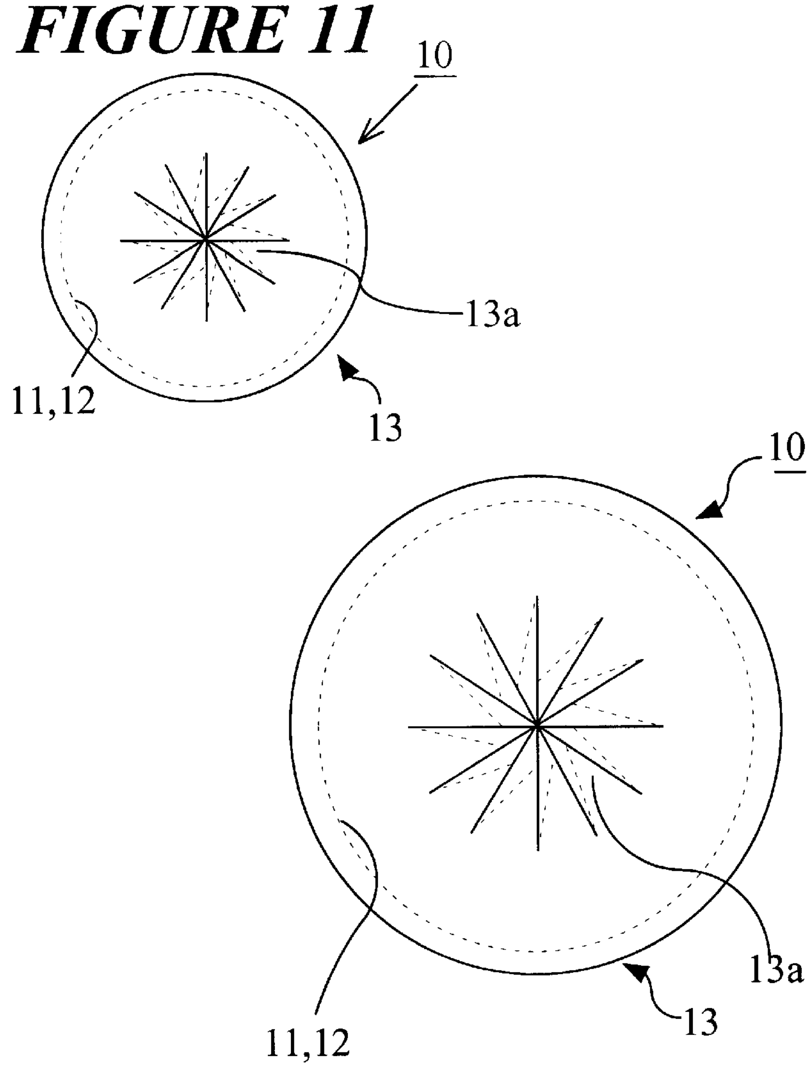
FIGURE 3A
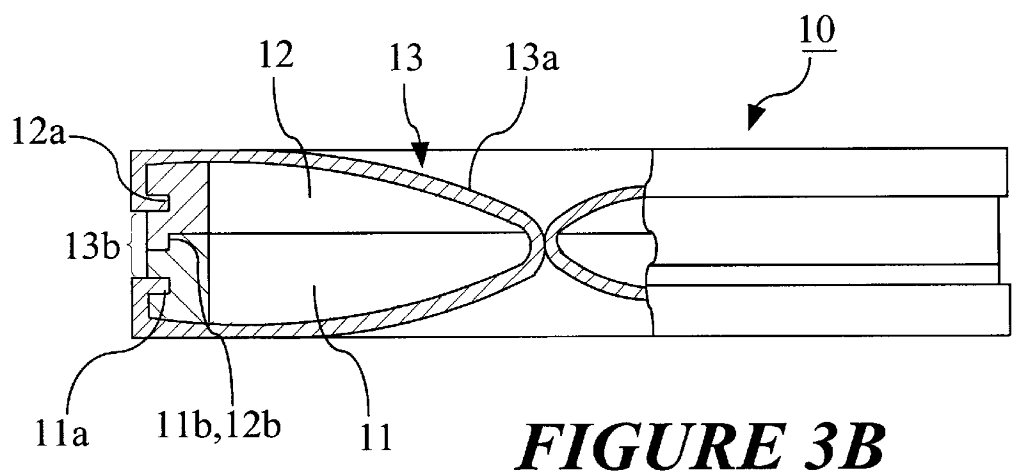
FIGURE 3B 11b,12b
12
13
13a
100D
12a
10
13b
11a
11
120
11b.,12b
12
13
13a
12a
10
13b
11a
11
110
111
112
130

VALVE AND VALVED TROCAR JACKET TUBE

BACKGROUND OF THE INVENTION

The present invention relates to a valve and a valved trocar jacket tube used in endoscopic surgery in pneumoperitoneum.

FIG. 1 shows a conventional valved trocar jacket tube wherein the valved trocar jacket tube 1 is composed of a cylindrical jacket 2 and a casing 3 secured to the top of the jacket 2. The casing 3 has a circular opening 3*a* on the upper part thereof. Furthermore, the casing 3 contains a valve 4 for opening and closing the opening 3*a* and a spring 5 for urging the valve 4 towards the closing direction therein.

In the case when the valved trocar jacket tube 1 thus constituted is employed, as shown in FIG. 2, a physician inserts the jacket 2 of the valved trocar tube 1 in a site, for example, the incised portion of the abdomen Pa of a patient P being an object to be operated. In case of using a clamp or the like, an adapter 6 being called by the name of reducer or introducer composed of a leakage preventing valve 6A having an opening 6*a* the inside diameter of which corresponds to the outside diameter of the clamp or the like and an outer cylinder 6B is employed. The physician sets the clamp or the like having a diameter corresponding to the diameter of the opening 6*a* of the adapter 6 thereto, and the clamp or the like so arranged is inserted through the opening 3*a* of the casing 3. In this case, the valve 4 is opened against the spring force of the spring 5 due to insertion of the adapter 6. As a result, leakage of an inert gas injected into an abdominal cavity for conducting easily endoscopy and the like is prevented.

According to the conventional valved trocar jacket tube 1, however, there is such a problem that since the diameter of the opening 3*a* defined on the casing 3 is stationary, it is required to use an adapter 6 having the diameter corresponding to that of the clamp or the like 7 to be employed on all such occasions, and such substituting operation required incidentally is troublesome, so that the operator's manipulation is prevented.

Furthermore, there are such problems that since any contour in the opening 6*a* of an adapter 6 is circular, the contour of a clamp or the like 7 is limited to that having a circular shape and that since the standard sizes in the opening 6*a* of an adapter 6 are usually 5, 10, and 12 mm, a clamp or the like 7 having an intermediate size such as 6 mm or 8 mm cannot be used, so that sizes of the clamp or the like 7 are also restricted.

Besides, since the inside diameters in the openings 6*a* of adapters 6 and the outside diameters of clamps or the like are nominal values, respectively, there are such problems that the inside diameter of an adapter 6 does not match with the outside diameter of a clamp or the like 7 in reality, and as a result, either such clamp or the like 7 is impossible to use or there is a case of arising leakage.

SUMMARY OF THE INVENTION

Accordingly, an object of the present invention is to provide a valve and a valved trocar jacket tube by which the use of an adapter becomes unnecessary, types of clamps and the like to be employed are not limited, and the leakage of an inert gas from an abdominal cavity can be prevented.

According to the first feature of the present invention, a valve disposed on the trocar jacket tube mounted to the incised portion of a diseased part, comprises a pair of rings placed oppositely in a coaxial state and a cylindrical elastic member the ends of which are attached respectively to said pair of rings and having an opening of a prescribed sectional area; said elastic member having such structure that when said pair of rings are rotated relatively in the opposite directions at a predetermined angle, said opening changes the sectional area between a closed state and a state of said prescribed sectional area in response to said predetermined angle.

According to the above described constitution, when the pair of rings are relatively rotated in the opposite directions at a predetermined angle from the state where the opening of the elastic member has been closed, the opening of the elastic member is opened. In case of employing a clamp or the like, it is inserted into an abdominal cavity through the above described opened opening. Since the elastic member has elasticity, the opening is close together with the clamp or the like inserted.

According to the second feature of the present invention, a valved trocar jacket tube mounted to the incised portion of a diseased part, comprises a pair of rings placed oppositely in a coaxial state; and a cylindrical elastic member the ends of which are attached respectively to said pair of rings and having an opening of a prescribed sectional area; said elastic member being provided with a valve having such structure that when said pair of rings are rotated relatively in the opposite directions at a predetermined angle, said opening changes the sectional area between a closed state and a state of said prescribed sectional area in response to said predetermined angle and a jacket means attached to either ring of said pair of rings and being inserted into said incised portion of the diseased part to maintain the same in an opened state.

BRIEF DESCRIPTION OF THE DRAWINGS

The invention will be described in more detail in conjunction with appended drawings, wherein:

FIG. 3A is a plan view showing the valve according to the present invention;

FIG. 3B is a sectional view of FIG. 3A;

FIG. 11 is a plan view showing a further embodiment of the valve of the present invention.

DESCRIPTION OF THE PREFERRED EMBODIMENTS

Figure 1:
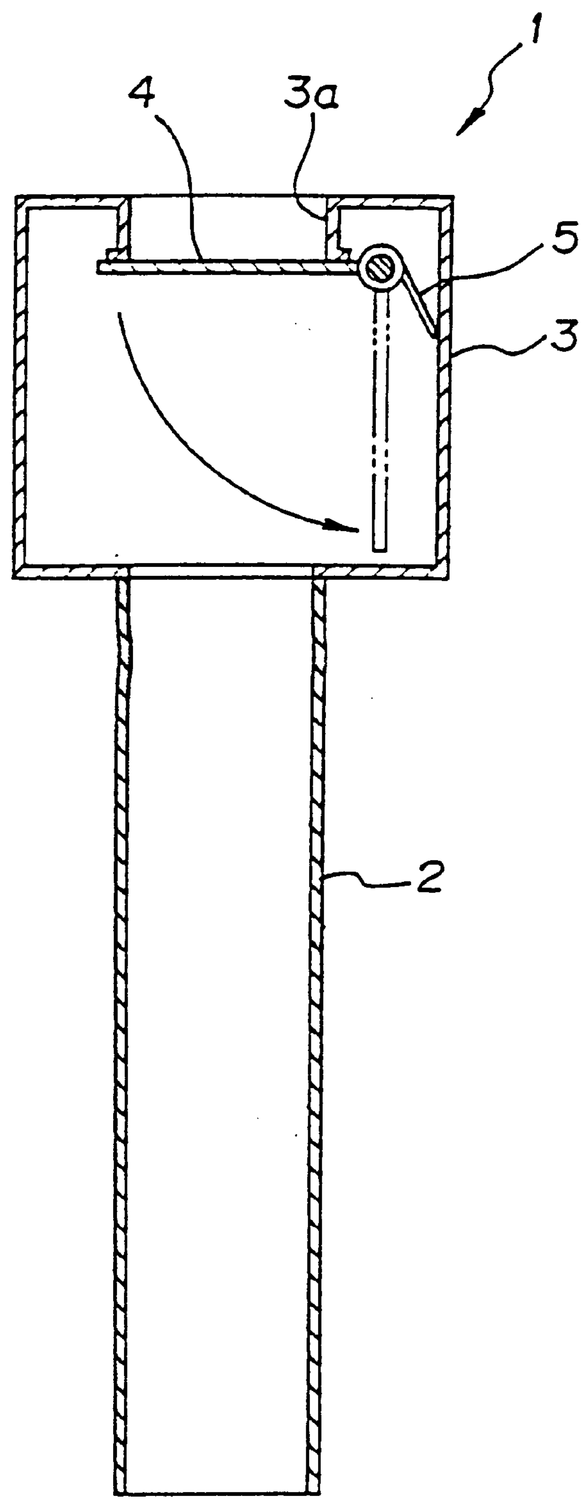
FIG. 1 is a sectional view showing a conventional valved trocar jacket tube.

The preferred embodiments of the present invention will be described in detail hereinafter by referring to the accompanying drawings.

FIGS. 3A and 3B are a plan view and a sectional view each showing the valve according to the preferred embodiment of the present invention wherein a valve 10 is composed of a pair of a male ring 11 and a female ring 12 placed oppositely and a cylindrical rubber-like member 13 functioning as an elastic member the ends of which are attached to the pair of the rings 11 and 12, respectively.

The pair of the rings 11 and 12 are prepared from a corrosion-resistant material such as metals, for example, stainless steel (SUS304, 316 etc.) titanium, titanium alloys, aluminum, and aluminum alloys; ceramics; and high polymeric organic materials. Grooves 11*a* and 12*a* into which is fitted an end portion 13*b* of the rubber-like material 13 which will be described hereunder are defined on the outer circumference of the pair of the rings 11 and 12, respectively. Furthermore, on the sides of the opposed pair of the rings 11 and 12 are defined stepped portions 11*b* and 12*b* being slid with each other. The pair of the rings 11 and 12 are arranged in such that they are rotatable relatively in the opposite directions due to the guiding action of the stepped portions 11*b* and 12*b*. Moreover, the pair of the rings 11 and 12 are formed into somewhat elliptical shape, as shown in FIG. 11, so that when either of the rings 11 or 12 is rotated at a prescribed angle, for example, 15° in either direction, they are adapted to be braked. The outside diameters of the pair of the rings 11 and 12 may be selected in response to the outside diameter of a member to be inserted in the valve 10. It is preferred that an outside diameter is around 100 mm in case of inserting an operator's hand into the valve, and it is around 30 mm in case of insertion of only a clamp or the like.

Figure 2:
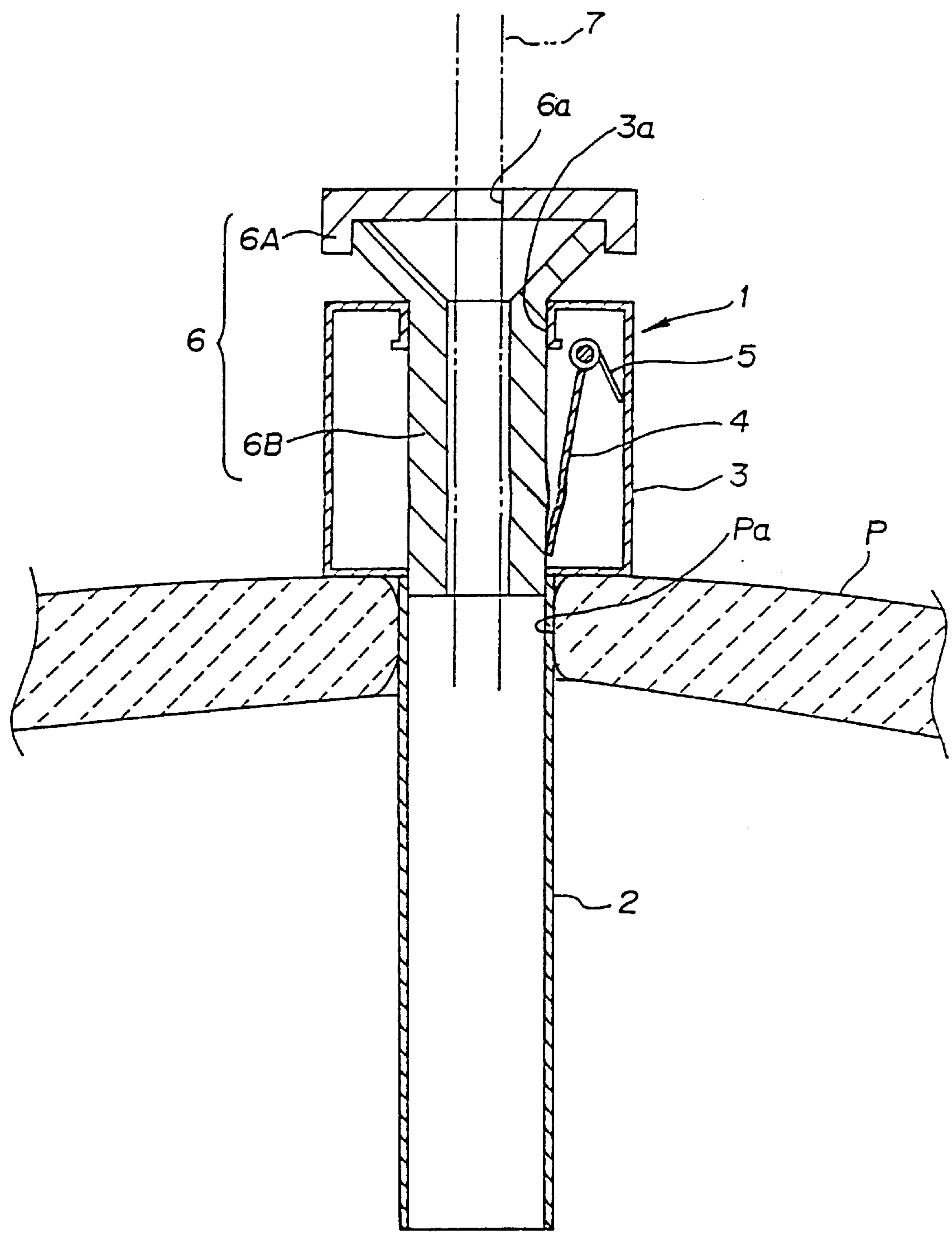
FIG. 2 is a sectional view showing a conventional valved trocar jacket tube as used.

The rubber-like member 13 is constituted in such that a cylindrical section 13*a* of the rubber-like member 13 is closed or opened when the pair of the rings 11 and 12 are relatively rotated in the opposite directions more specifically, the rubber-like member 13 is formed from a thin film having a thickness of around 30 to 50 mm and made from a material having elasticity such as natural rubber, synthetic rubber, polyvinyl chloride, silicone, and a variety of elastomers. The rubber-like member 13 includes an opening 13*c* having a predetermined cross-sectional area at the central portion thereof, and is shaped in such that the diameter of which decreases in the direction from the opposite ends to the central opening 13*c* of the rubber-like member 13 (see FIG. 2). Furthermore, convex portions 13*b* which are fitted in the grooves 11*a* and 12*a* of the pair of the rings 11 and 12 are formed on the opposed ends of the rubber-like member 13, so that the rubber-like member 13 is detachable from the grooves 11*a* and 12*a*. Because of such detachable structure of the rubber-like member 13, it can be easily replaced by a fresh one in the case when the used rubber-like member 13 is broken or on the like occasions.

Figure 4A:
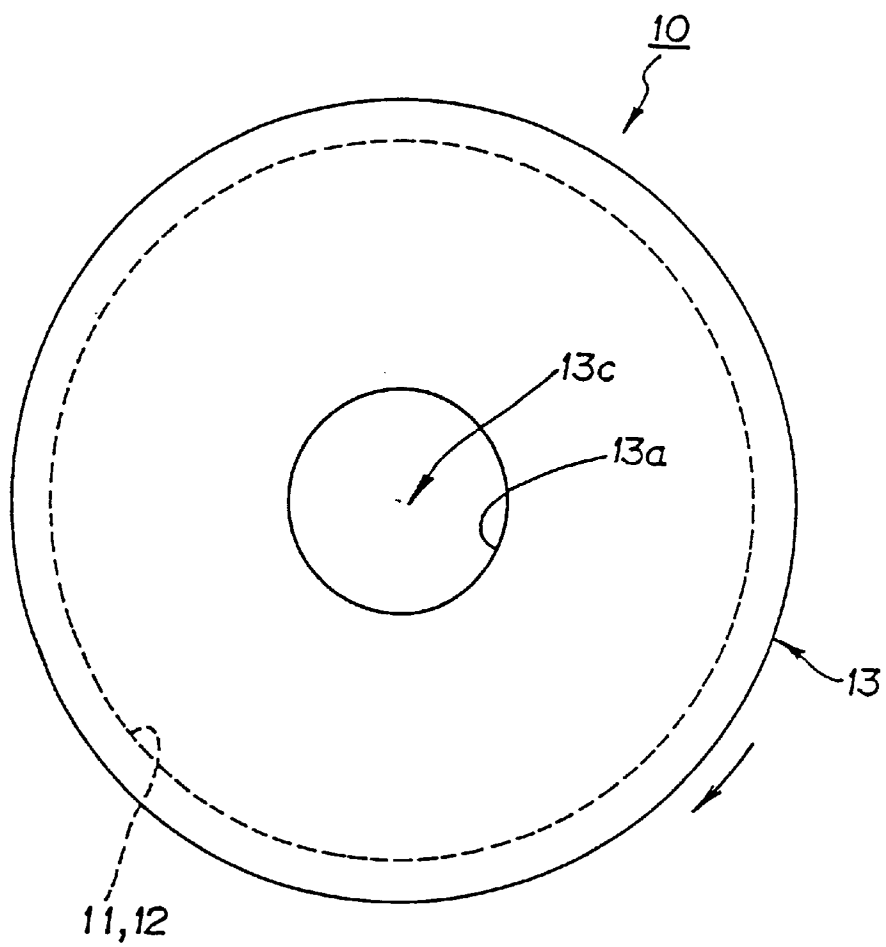
FIG. 4A is a plan view showing the opened state of the valve according to the present invention.
Figure 4B:
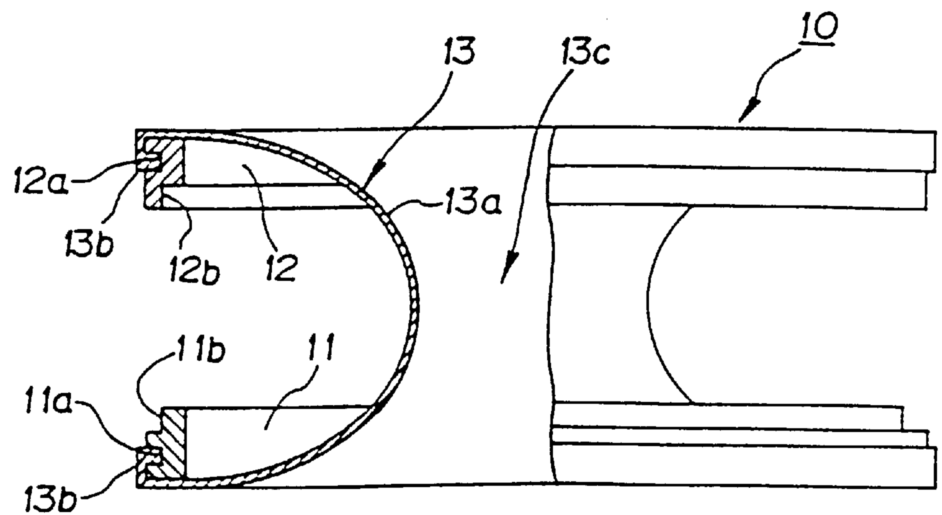
FIG. 4B is a sectional view of FIG. 4A.

FIGS. 4A and 4B are a plan view and a sectional view each showing an opened state for inserting a member to be inserted. In this case, when the female ring 12 is rotated at a predetermined angle, for example, 15° in either direction from the closed state of the cylindrical section 13*a* of the rubber-like member 13, the cylindrical section 13*a* is opened, while when the female ring 12 is rotated at 180°, the pair of the rings 11 and 12 come to be a separable state as shown in FIG. 4B. Furthermore, when the female ring 12 is rotated at 180° in the reverse direction, the pair of the rings 11 and 12 become a joined state as a result of their mutual attraction as shown in FIGS. 3A and 3B, even if they are separated from each other, so that the cylindrical section 13*a* is twisted to become a closed state.

Figure 5:
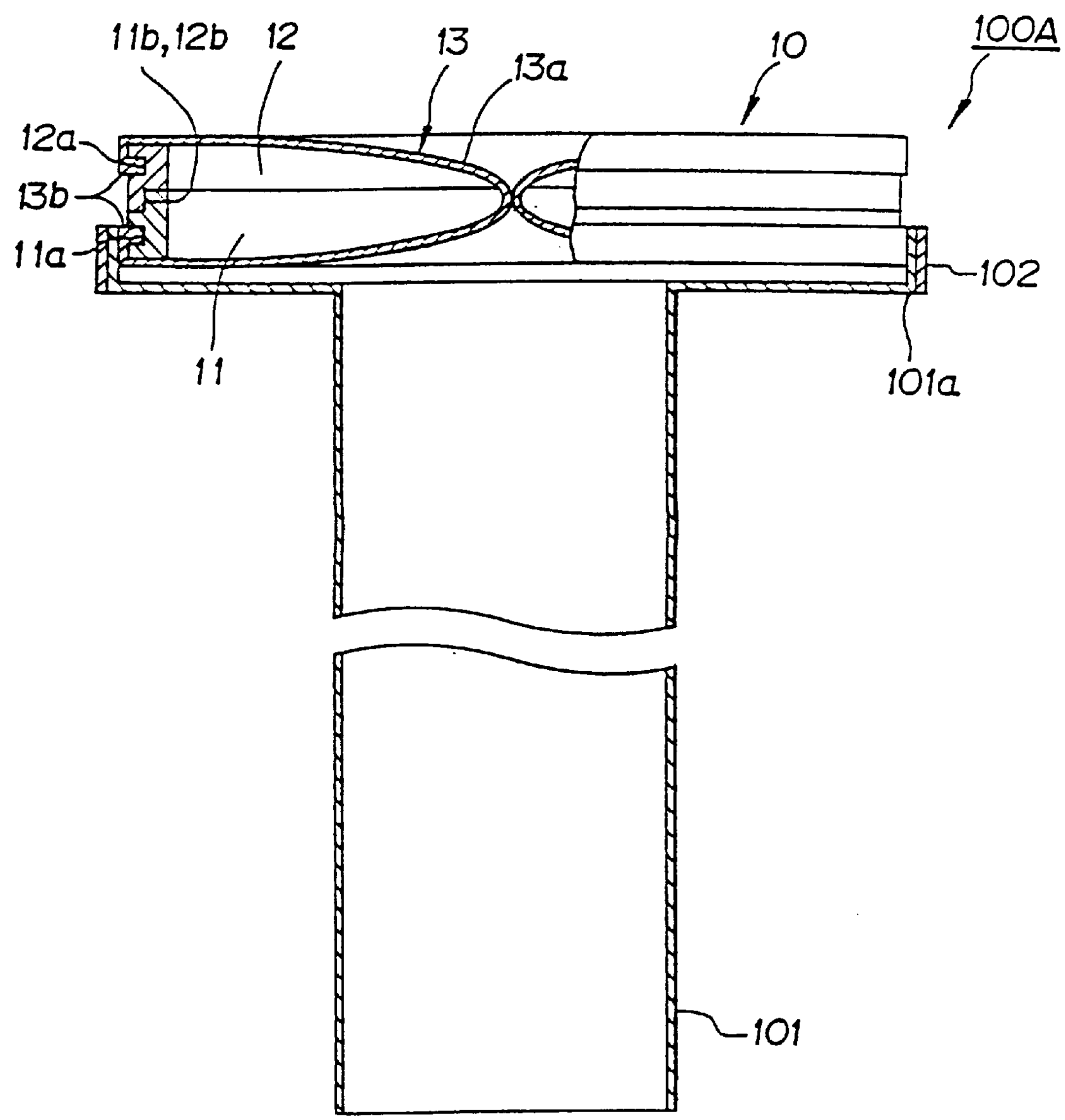
FIG. 5 is a sectional view showing the valved trocar jacket tube according to the first manner of practice of the present invention.

FIG. 5 is a sectional view showing the valved trocar jacket tube according to the first preferred embodiment of the present invention wherein the valved trocar jacket tube 100A is prepared by attaching a cylindrical jacket 101 having the inside diameter of, for example, 10 mm to the valve 10 shown in FIG. 3B including a pair of the rings 11 and 12 having the outside diameter of, for example, 30 mm. The jacket 101 is made of, for example, a plastic material such as polycarbonate plastic, and on the upper part of which is provided with a mounting section 101*a* on which is to be mounted the male ring 11, so that the male ring 11 is mounted on the mounting section 101*a* by means of a band 102.

Figure 6:
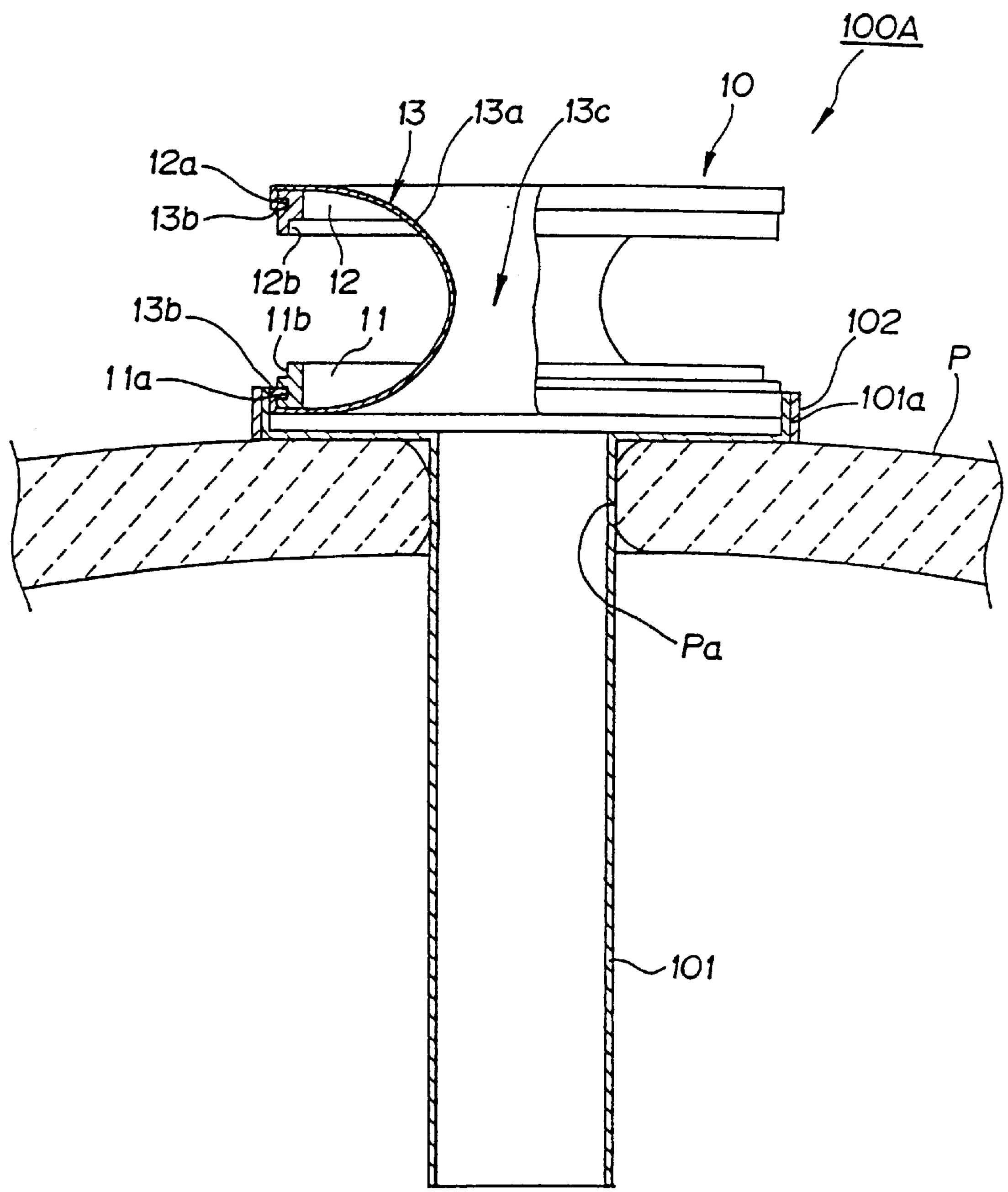
FIG. 6 is a sectional view showing the valved trocar jacket tube according to the first manner of practice of the present invention as used.

FIG. 6 is a sectional view showing the valved trocar jacket tube 100A according to the first preferred embodiment of the invention as used wherein a physician inserts the jacket 101 into the incised portion of the diseased part, for example, the incised portion of the abdomen Pa of a patience P being an object to be operated. In this case, when the female ring 12 is rotated at a predetermined angle, for example, 15° in either direction from the closed state of the cylindrical section 13*a* of the rubber-like member 13, the cylindrical section 13*a* is opened. In case of employing a clamp or the like, the physician inserts such clamp or the like in the abdominal cavity through the opened cylindrical section 13*a* and the jacket 101.

According to the valved trocar jacket tube 100A of the first manner of practice in the present invention, since the rubber-like member 13 has elasticity, it is flexibly close together with the clamp or the like used for the surgery in celiotomy, whereby types of the clamp or the like to be used are not restricted, so that such clamps or the like having other contours than circular contour and those having intermediate sizes which have never been employed heretofore in the surgery in celiotomy can also be used. Hence, there is no need of an adapter called by the name of reducer or introducer. On one hand, when the female ring 12 is rotated up to a predetermined angle, the rotation thereof is braked, so that it is prevented that the opening in the cylindrical section 13*a* of the rubber-like member 13 becomes too wide, whereby leakage of an inert gas from the abdominal cavity can be prevented. Moreover, the inside and the outside of an abdominal cavity which is isolated with the abdominal border can be positively shut off. Furthermore, a needle for centesis or a clamp and the like having the outside diameter of less than 10 mm which could have been not utilized in a conventional valved trocar jacket tube so far as an adapter inevitably used at the same time becomes possible to use, since the rubber-like member 13 is close together with such needle, clamp or the like to close the gap defined around the latter.

Figure 7:
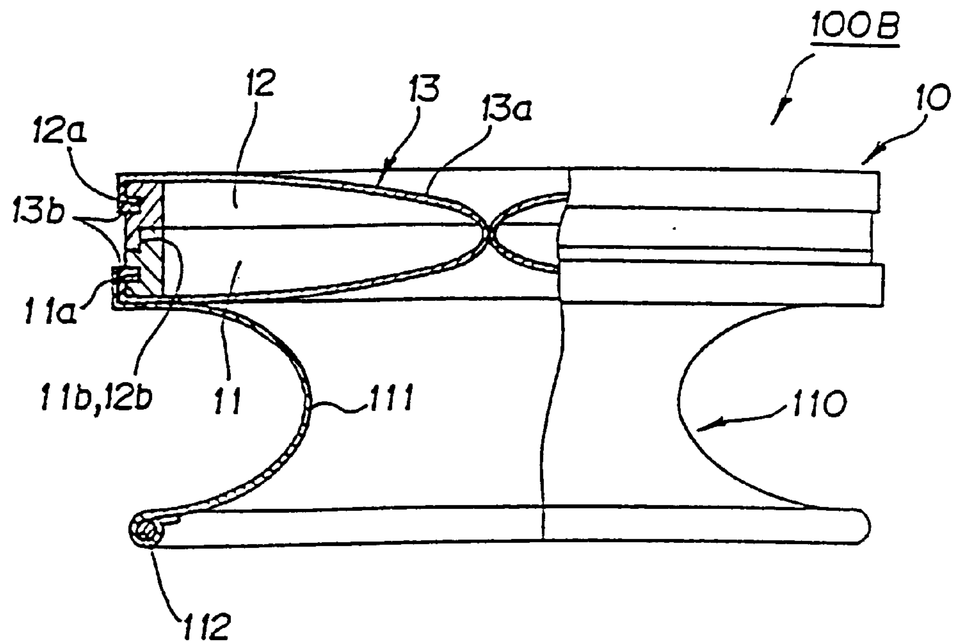
FIG. 7 is a sectional view showing the valved trocar jacket tube according to the second preferred embodiment of the present invention.

FIG. 7 is a sectional view showing the valved trocar jacket tube according to the second of preferred embodiment the invention wherein the valved, trocar jacket tube 100B is prepared by adding a skirt 110 to the valve 10 shown in FIGS. 3A and 3B provided with a pair of the rings 111 and 12 having the outside diameter of, for example, 100 mm. The skirt is composed of a cylindrical member 11 made of rubber or the like having the thickness of around 100 mm and having a contour the diameter of which decreases from both the upper and lower ends towards the central portion thereof and a circular ring-shaped resilient member 112 having the outside diameter of, for example, 100 mm and attached to the lower end of the cylindrical member 111. The upper end of the cylindrical member 111 is bonded or fused in the vicinity of the convex portion 13*b* which is fitted into the groove 11*a* of the male ring 11 in the rubber-like member 13. Alternately, the upper end of the cylindrical member 111 may have such a constitution that it is fitted into the groove 11*a* of the male ring 11. In accordance with the arrangement as described above, in the case, for instance, when a skirt 110 is broken, the used skirt can easily be replaced by another fresh skirt 110. The ring-shaped resilient member 112 is prepared by covering a resilient material such as a spring coil, and a spring with a nylon elastomeric resin.

Figure 8:
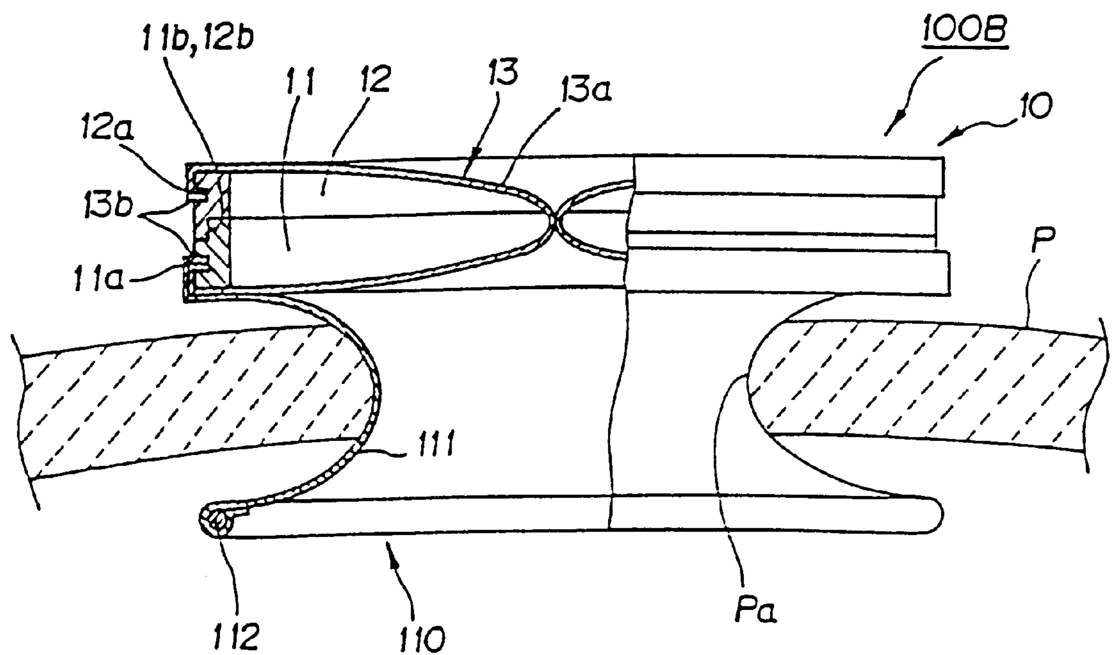
FIG. 8 is a sectional view showing the valved trocar jacket tube according to the second preferred embodiment of the present invention as used.

FIG. 8 is a sectional view showing the valved trocar jacket tube 100B according to the second preferred embodiment in the invention as used wherein in case of mounting the valved trocar jacket tube 100B, the under side of the skirt 110 is inserted into the body of a patient P through the incised portion of the abdomen Pa thereof while forcing the circular ring-shaped resilient member 112 in such that the contour thereof is kept in a slender elliptical shape. Thereafter, the ring-shaped resilient member 112 expands into the circular configuration in the abdominal cavity to engage with the incised portion of the abdomen Pa.

According to the valved trocar jacket tube 100B of the second preferred embodiment in the present invention, the skirt 110 is close together with the peritoneum due to the tension thereof to be capable of maintaining hemostasis and airtightness. Furthermore, there is no need of an adapter called by the name of reducer or introducer. Besides, even if a physician's hand is inserted in the abdominal cavity, the rubber-like member 13 is close together with the hand, so that leakage of an inert gas in the abdominal cavity in this occasion can be suppressed to the minimum. In addition, when a physician conducts, for example, an operation on a patient's organ by inserting directly his (or her) hands through the incised portion of the abdomen Pa, the physician's hands contact strongly with the patient's peritoneum in the incised portion Pa. In this case, however, such strong contact can be avoided by the use of the rubber-like member 13.

Figure 9:
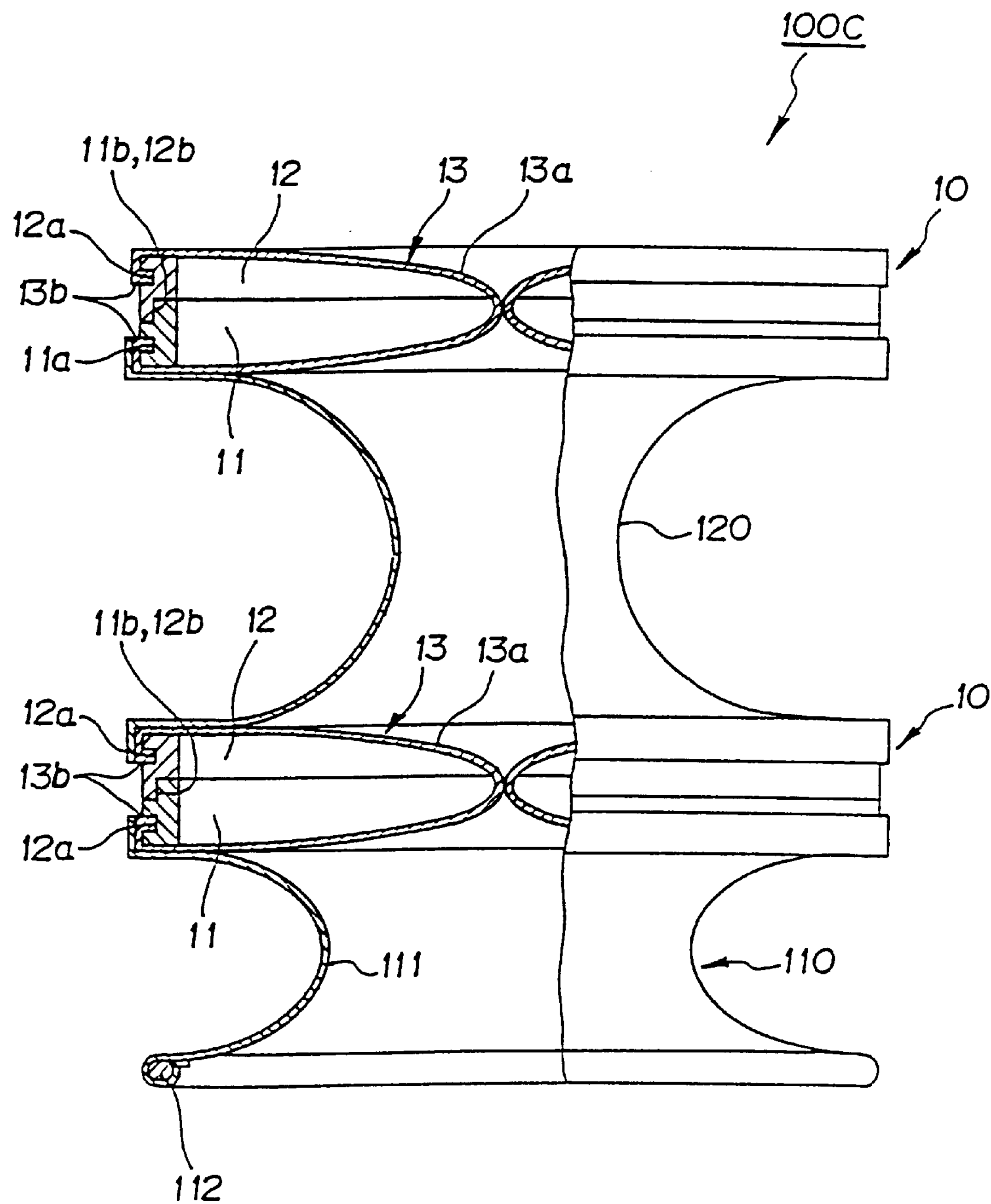
FIG. 9 is a sectional view showing the valved trocar jacket tube according to the third preferred embodiment of the present invention.

FIG. 9 is a sectional view shoving the valved trocar jacket tube according to the third preferred embodiment of the present invention wherein the valved trocar jacket tube 100C is prepared by placing one valve 10 provided with a pair of the rings 11 and 12 shown in FIGS. 3A and 3B having the outside diameter of, for example, 100 mm over another valve 10, connecting these two valves 10, 10 with a connecting cylinder 120, and adding the same skirt 110 as that of the second manner of practice to the under side of the lower valve 10. The upper end of the connecting cylinder 120 is bonded or fused in the vicinity of the convex portion 13*b* which is fitted into the groove 11*a* of the male ring 11 contained in the upper valve 10, while the lower end of the connecting cylinder 120 is bonded or fused in the vicinity of the convex portion 13*b* which is fitted into the groove 12*a* of the female ring 12 contained in the lover valve 10. In the skirt 110, the upper end of the cylindrical member 111 is bonded or fused in the vicinity of the convex portion 13*b* fitted into the groove 11*a* of the male ring 11 contained in the lower valve 10 as in the case of the second manner of practice. It is to be noted that the connecting cylinder 120 and the skirt 110 may be detachable from one another for easy exchange thereof.

According to the valved trocar jacket tube 100C, first, the upper valve 10 is opened to insert an instrument (instruments) or a hand (hands) through the same, and the upper valve 10 is closed, thereafter, the lower valve 10 is opened to insert the instrument or the hand through the same. In this case, even if the lower valve 10 is opened, since the gap defined by the inserted instrument or hand is close together with the upper valve 10, leakage of the inert gas existing in the abdominal cavity as a result of application of aeroperitoneum can be suppressed to the minimum.

Figure 10:
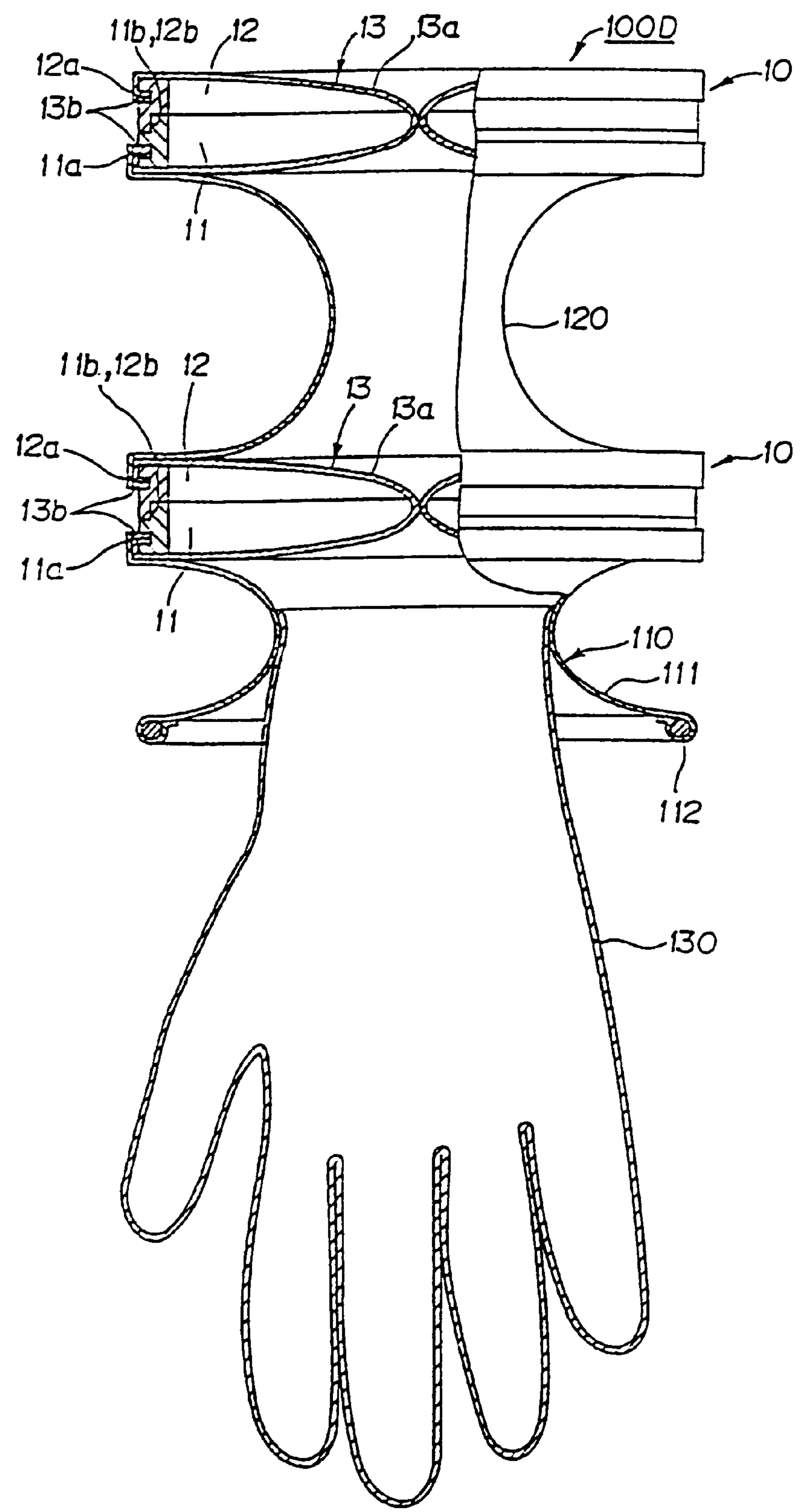
FIG. 10 is a sectional view showing the valved trocar jacket tube according to the fourth preferred embodiment of the present invention.

FIG. 10 is a sectional view showing the valved trocar Jacket tube according to the fourth preferred embodiment the present invention wherein the valved trocar jacket tube 100D is prepared by adding a glove 130 to the third manner of practice. The glove 130 is bonded or fused to the central position of the cylindrical member 111 of the skirt 110 inside the same.

As a result of adding the glove 130, the manipulation in the abdominal cavity can be performed with the use of the glove 130 attached to the jacket tube 100D, but not with use of the glove worn on a physician's hand who conducts endoscopic surgery operation, so that the endoscopic surgery operation can be smoothly continued in a clean condition without contaminating the glove worn at the time when the operation is started.

It is to be noted that the present invention is not limited to the above described manners of practice, but a variety of manners of practice may be applied. For instance, the glove 130 may be added to the second manner of practice as in the case of the fourth manner of practice. Furthermore, a combination of concave and convex grooves may be added to a pair of the male and female rings 11 and 12, so that they can be rotated, but cannot be separated upwards and downwards from each other.

As described above, according to the present invention, since the opening of an elastic member is opened or closed by rotating a pair of rings to which is attached the elastic member, the elastic member is close together with a clamp or the like to be inserted into an abdominal cavity through the opened opening. As a result, types of clamps and the like are not restricted in surgery operation. Furthermore, such clamps or the like those having other contours than circular contour as well as those having intermediate sizes which could have been not utilized heretofore come to be possible to use. Moreover, since there is no need of an adapter, the operation for exchanging the adapter is not necessary, so that the surgery in celiotomy can be smoothly performed. Besides, leakage of an inert gas from the abdominal cavity can be prevented.

Although the invention has been described with respect to specific embodiment for complete and clear disclosure, the appended claims are not to be thus limited but are to be construed as embodying all modification and alternative constructions that may be occurred to one skilled in the art which fairly fall within the basic teaching here is set forth.

What is claimed is:

1. A valve disposed on a trocar jacket tube mounted to an incised portion of a diseased part, comprising:

a pair of coaxially aligned elliptical rings; and a cylindrical elastic member including ends attached respectively to said pair of rings and an opening having a prescribed sectional area;

said pair of rings being capable of rotating in opposite directions relative to one another to a predetermined angle, whereby said opening changes between a closed state and said prescribed sectional area in response to ring rotation to said predetermined angle.

2. The valve defined in claim 1 further including a jacket means attached to either ring of said pair of rings and disposed within the incised portion of the diseased part to maintain the incised portion in an opened state.

3. The valve defined in claim 1, wherein said pair of rings are adjacent.

4. The valve defined in claim 3, wherein said pair of rings further comprise mating stepped portions, whereby said stepped portions guide the rings during rotation.

5. A valve disposed on a trocar jacket tube mounted to an incised portion of a diseased part, comprising:

a pair of coaxially aligned rings, wherein said pair of rings comprise ring-shaped sliding sections which slide mutually when said pair of rings are rotated to said predetermined angle, and said ring-shaped sliding sections have an elliptical contour; and a cylindrical elastic member including ends attached respectively to said pair of rings and an opening having a prescribed sectional area;

said pair of rings being capable of rotating in opposite directions relative to one another to a predetermined angle, whereby said opening changes between a closed state and said prescribed sectional area in response to ring rotation to said predetermined angle.

6. A valved trocar jacket tube mounted to an incised portion of a diseased part, comprising:

a pair of rings coaxially aligned elliptical, and a cylindrical elastic member including ends attached respectively to said pair of rings and an opening having a prescribed sectional area; and said elastic member and rings forming a first valve that operates when either of said pair of rings is rotated relatively to a predetermined angle, said opening changes between a closed state and the prescribed sectional area in response to ring rotation to said predetermined angle, and a jacket means attached to either ring of said pair of rings and adapted to be placed within the incised portion to maintain the incised portion in an opened state.

7. The valved trocar jacket tube as defined in claim 6 further comprising a second valve connected to said first valve by a connecting member.

8. The valved trocar jacket tube as defined in claim 6 wherein said jacket means is provided with a ring-shaped resilient member which expands wider than the incised portion of the diseased part when inserted into the incised portion, and a ring-shaped cylindrical member the ends of which are attached to either one of said pair of rings and said ring-shaped resilient member, respectively.

9. The valved trocar jacket tube as defined in claim 8 wherein said first valve is connected to a second valve by a connecting member.

10. The valved trocar jacket tube as defined in claim 8 wherein said resilient member includes a glove.

11. The valved trocar jacket tube defined in claim 6, wherein said jacket means comprises a cylindrical plastic tube.

12. The valved trocar jacket tube of claim 3 wherein said jacket means includes:

a skirt of an elastic material attached at one end to one of said pair of rings; and a ring-shaped resilient member attached to the other end of said skirt, said ring-shaped resilient member capable of expanding wider than the incised portion of the diseased part when inserted into the incised portion.

13. The valved trocar jacket tube of claim 3, wherein the cross-sectional area of said jacket means between the one end and the other end is smaller than cross-sectional areas at the one end and the other end thereof.

14. A valved trocar jacket tube mounted to an incised portion of a diseased part, comprising:

a pair of rings coaxially aligned, wherein said pair of rings include ring-shaped sliding sections which slide mutually when said pair of rings are rotated to said predetermined angle, and said ring-shaped sliding sections have an elliptical contour;

a cylindrical elastic member including ends attached respectively to said pair of rings and an opening having a prescribed sectional area; and said elastic member and rings forming a first valve that operates when either of said pair of rings is rotated relatively to a predetermined angle, said opening changes between a closed state and the prescribed sectional area in response to ring rotation to said predetermined angle, and a jacket means attached to either ring of said pair of rings and adapted to be placed within the incised portion to maintain the incised portion in an opened state.

* * * * *

UNITED STATES PATENT AND TRADEMARK OFFICE

CERTIFICATE OF CORRECTION

PATENT NO. :6,110,154
DATED :August 29, 2000
INVENTOR(S) :Shimomura et al

It is certified that error appears in the above-identified patent and that said Letters Patent is hereby corrected as shown below:

On the title page, item [73] Assignee; should read --Hakko Medical, Co., Ltd --

Signed and Sealed this

Twenty-sixth Day of December, 2000

Attest:

Q. TODD DICKINSON

*Attesting Officer* *Director of Patents and Trademarks*